United States Patent [19]

Zimmerman

[11] 4,152,073
[45] May 1, 1979

[54] LIQUID AND GAS CHLORINE DIOXIDE PHOTOMETER

[75] Inventor: William E. Zimmerman, Covington, Va.

[73] Assignee: Westvaco Corporation, New York, N.Y.

[21] Appl. No.: 809,077

[22] Filed: Jun. 22, 1977

[51] Int. Cl.$^2$ ............................................. G01N 21/06
[52] U.S. Cl. ................................. 356/436; 250/573; 356/410; 356/246
[58] Field of Search ............... 356/201, 205, 181, 184, 356/203, 246, 183; 250/573 C, 343; 162/236, 47; 68/5; 23/232

[56] References Cited

U.S. PATENT DOCUMENTS

| | | | |
|---|---|---|---|
| 2,690,695 | 10/1954 | Coates | 356/246 |
| 3,062,963 | 9/1960 | Douty | 356/181 |
| 3,572,994 | 3/1971 | Hochstrasser | 356/181 |
| 3,797,942 | 3/1974 | Joly | 356/181 |
| 3,814,664 | 6/1974 | Carlsmith | 162/236 |
| 3,977,830 | 8/1976 | Topol | 356/181 |

*Primary Examiner*—John K. Corbin
*Assistant Examiner*—B. Wm. de los Reyes
*Attorney, Agent, or Firm*—W. Allen Marcontell; Ernest B. Lipscomb, III

[57] ABSTRACT

The density of chlorine dioxide gas in a wet acid atmosphere may be continuously monitored with a photometer energized by a constant voltage incandescent light source illuminating a 0.5 inch thickness, continuous flow sample spaced between quartz glass windows. The emergent light is filtered to pass approximately 4400 Angstrom wavelength light to a selenium photocell. Photocell power output measuring means is calibrated to correspond with chlorine dioxide gas density. The concentration strength of an aqueous solution of chlorine dioxide is continuously monitored with a similar photometer having a 0.125 inch sample space between windows and a 4600 Angstrom filter for the emergent light.

9 Claims, 4 Drawing Figures

LIQUID AND GAS CHLORINE DIOXIDE PHOTOMETER

BACKGROUND OF THE INVENTION

1. Field of the Invention

The present invention relates to photometric analysis of chemical processes and products.

More particularly, the present invention relates to photometric techniques for continuously monitoring the process efficiency and product strength of a chlorine dioxide generation plant.

2. Description of the Prior Art

Dilute solutions of chlorine dioxide are used by the pulp and paper industry as an extremely effective bleaching compound due to reactive perference thereof for lignin in lieu of cellulose. However, due to the explosive nature of the gas, it must be generated at the point of use and stored and used in dilute aqueous solutions.

Continuous generation of chlorine dioxide by means of the Mathieson Process, for example, follows a complex reaction series occurring from contacting a gaseous mixture of air and sulfur dioxide with a liquid solution of sodium chlorate and sulfuric acid in a sparging vessel. The process is highly exothermic and therefore the generator must be externally cooled to maintain a safe gaseous chlorine dioxide product temperature below 57° C. (135° F.).

The warm gas is drafted at 2 to 6 inches of water vacuum from a volumetric void where it is collected at the top of the gas/liquid contact sparging vessel into the bottom of a counterflow absorber vessel. Cascading chilled water, approximately 4° C. (40° F.), absorbs the upflowing gas into a dilute aqueous solution of approximately 8 to 9 grams per liter of water.

Although the material flow balance is adjusted to yield an end product of the desired solution strength, numerous events may upset the balance. For example, an increase in the absorber supply water temperature will reduce the absorption rate thereby permitting an undissolved portion of the generated gas to be exhausted to the atmosphere through the draft fan at the top of the absorber vessel. Although the end product solution strength is batch analyzed chemically at relatively frequent intervals, hourly for example, upsets of the nature described may develop in a matter of minutes. Consequently, it is highly desirable to maintain continuous surveillance over the process in both the gaseous and liquid stages.

In the past, no surveillance was exercised over the gaseous stage of chlorine dioxide generation. Since an aqueous solution of the compound will vary in color from pale yellow to yellow-brown in generally direct proportion to increased concentration, liquid concentration has been monitored by means of a colorimeter. However, large changes in concentration are required to produce a change in color hue of such magnitude as to be discernible by the colorimeter technique. Consequently, the technique has proven unsatisfactory due to insensitivity.

It is well known that chlorine dioxide is highly absorptive of infra-red spectrum light of greater than 7000 Angstroms wavelength. Such properties are exhaustively reported by authors A. H. Nielsen and P. J. H. Woltz in The Journal Of Chemical Physics, Volume 20, Number 12, December, 1952. Although laboratory apparatus has been devised to measure vaporous chlorine dioxide, such apparatus cannot be used to measure concentration of the compound in aqueous solutions since the water phase of the solution absorbs a significantly greater portion of the infrared spectrum than chlorine dioxide. Moreover, such vapor measuring apparatus is extremely environmental sensitive and consequently unsuitable for harsh industrial conditions.

Chlorine dioxide is also known to have an ultraviolet or blue spectral absorption band centered at approximately 3600 Angstroms. However, for reasons to be subsequently explained, this ultraviolet absorptive property of chlorine dioxide may not be readily exploited in an industrial environment for the present objective of concentration surveillance.

It is, therefore, an objective of the present invention to teach a method and apparatus for detecting small changes in the concentration of chlorine dioxide in dilute solution with water.

Another object of the present invention is to provide a method and apparatus for the surveillance of gaseous chlorine dioxide.

These and other objects of the invention will become apparent from the following description.

SUMMARY OF THE INVENTION

Briefly, the present invention comprises a sample fluid flow line connected in parallel with the monitored production flow stream. At a convenient location along the sample flow line is provided a photometric sensing unit. Each sensing unit comprises a pair of transparent quartz glass window plates having a void space therebetween to receive the sample flow. White light from a constant voltage incandescent source is passed through the windows and an appropriate filter on the emergent side. To monitor gaseous chlorine dioxide, a 4400 Angstrom filter may be used whereas a 4600 Angstrom filter serves the liquid solution of chlorine dioxide.

Light of the respective wavelength passing the filter is received by a selenium photocell to generate a variable electric potential proportional to the quantity or intensity of light received. Since gaseous chlorine dioxide is moderately absorptive of the 4400 Angstrom wavelength and likewise for the 4600 Angstrom wavelength to aqueous solutions of chlorine dioxide, a correlation may be drawn between the photocell voltage emission and the concentration quantity of chlorine dioxide within the sample stream.

BRIEF DESCRIPTION OF THE DRAWING

Relative to the drawing wherein like reference characters designate like or similar elements throughout the several figures.

DESCRIPTION OF THE PREFERRED EMBODIMENTS

Figure 1:
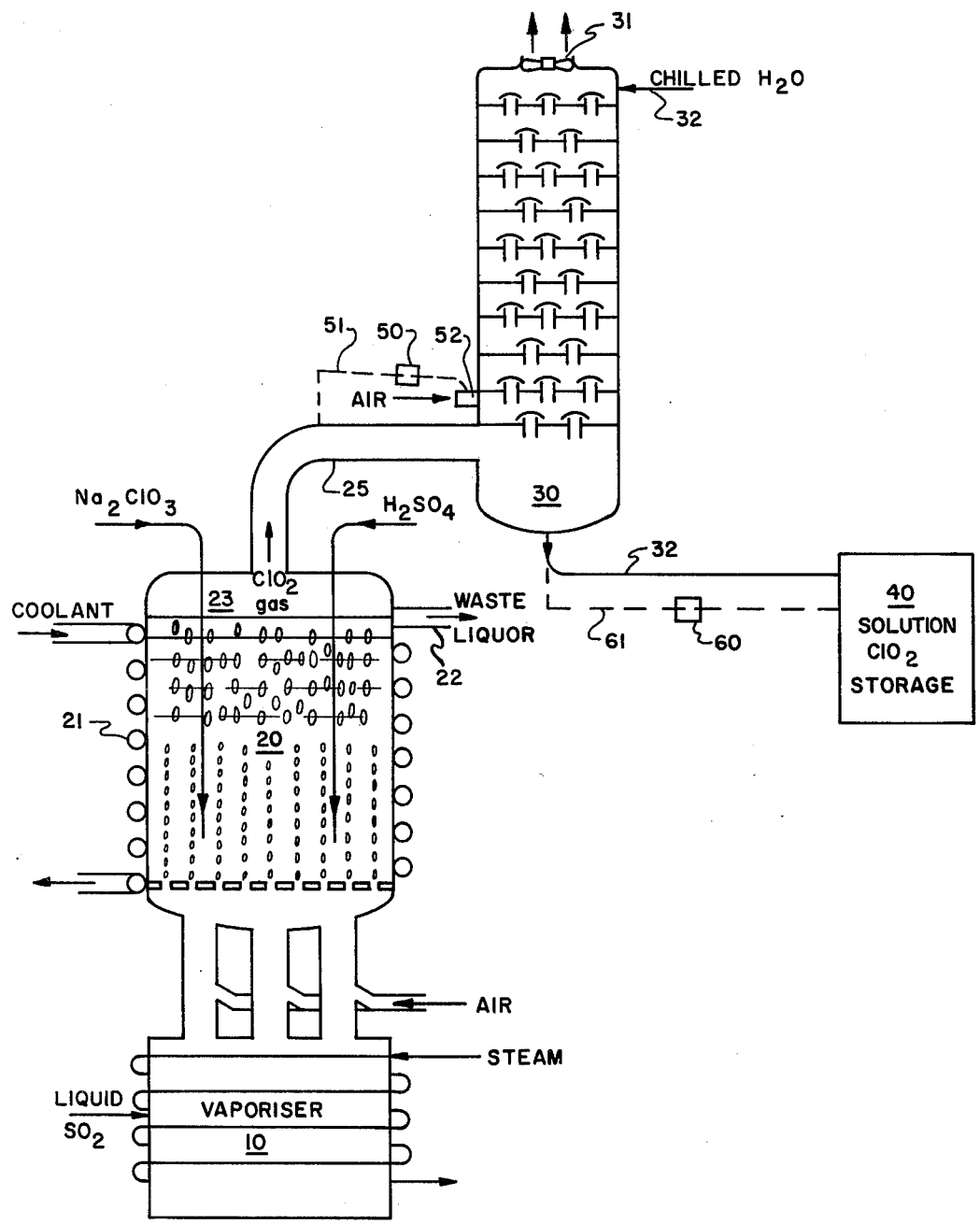
FIG. 1 is a schematic of a Mathieson Process chlorine dioxide generating plant showing relative positionment of the disclosed photometers.

With reference to FIG. 1, liquid sulfur dioxide is drawn from storage and pumped into a vaporizing vessel 10 where it is heated above the vapor point and combined with air. The vaporous mixture of sulfur dioxide and air is then conducted into the bottom of a sparging vessel 20 for gas-liquid contact with a liquid solution of sulfuric acid, sodium chlorate and water. Water circulating coils 21 around the vessel circumference carry away some of the exothermic heat of the reaction. Waste liquor from the reaction is drawn away by conduit 22 located near the upper end of the vessel 20 to maintain the liquid column height of the vessel.

Chlorine dioxide gas generated by the reactor is collected in the void volume 23 above the liquid level and drawn by pressure differential draft through a transfer duct 25 into the lower section of absorber tower 30. At the upper end of the absorber tower 30 is an induction fan 31 and the inlet of a chilled water conduit 32. Structure is provided between the upper and lower ends of the tower to enhance gas-liquid contacting as the water cascades down the tower and the chlorine dioxide gas rises.

At the lower extremity of the absorber tower 30 the resulting water-chlorine dioxide solution is drawn off for storage in an appropriate vessel 40 or directed to bleaching vats not shown.

To monitor the density of chlorine dioxide gas generated, the present invention taps the transfer duct 25 with a ¼ inch (0.64 cm) noncorrosive Teflon tube 51, which carries a sample flow stream through a photometric window head 50. Since the pressure head within the transfer duct 25 is maintained at modestly low levels, to induce flow it is necessary to aspirate the tubing 51 by means of an aspirator 52 powered by a low pressure, 3 psig, instrument air supply, for example. Discharge from the aspirator 52 may be into the absorber vessel 30 or to atmosphere.

Of particular note to the gas sample line 51 installation is the need for a large, straight-line slope in the line past the gas photometer 50. Due to the hot, complex acid atmosphere of the sparging vessel 20, compounds other than chlorine dioxide are vaporized and rise into the gas void 23. As the gas flow stream is rapidly cooled along the length of the sample line 51, some of these other compounds condense back to the liquid phase. When this condensate flows past the photometer window, it may upset the sensory system which is calibrated for gas. To avoid this undesirable result of condensate, the gas sample line 51 is maintained at a large slope, 30° for example, without sags or low points to keep the condensate uniformly dispersed in a thin flow stream along the line 51 bottom so it may be managed at the photometer in a manner subsequently described. Also, the elimination of sags in the line prevents the accumulation of this condensate in pools at low points which form a liquid seal to the low, aspirated pressure differential therethrough.

Line connections for the liquid concentration monitoring system are less critical than for the gas system since only one fluid phase is encountered. Accordingly, a conveniently routed ¼ inch Teflon tube 61 connected in parallel with the solution discharge line 32 from the absorber vessel 30 will carry an adequate, representative sample flow through the liquid photometer 60.

Figure 2:
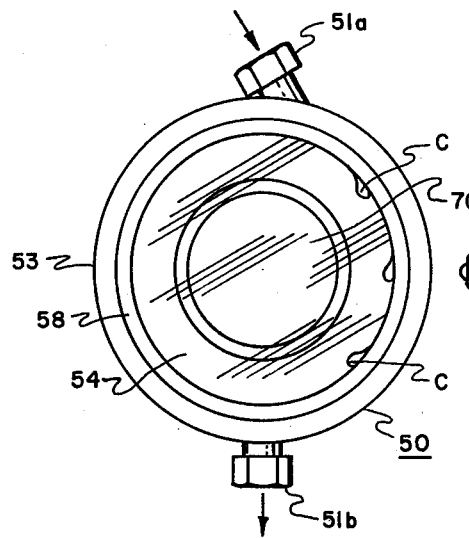
FIG. 2 is a frontal elevation of a photometer window unit of the present invention particularly adapted for gas density monitoring.
Figure 3:
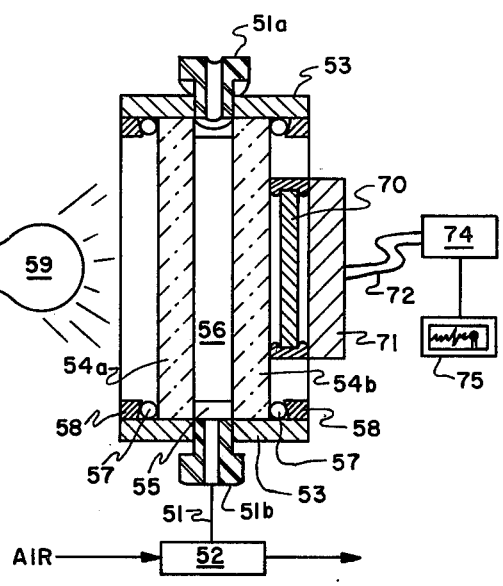
FIG. 3 is a sectional elevation of the gas density monitoring photocell window unit of the present invention.
Figure 4:
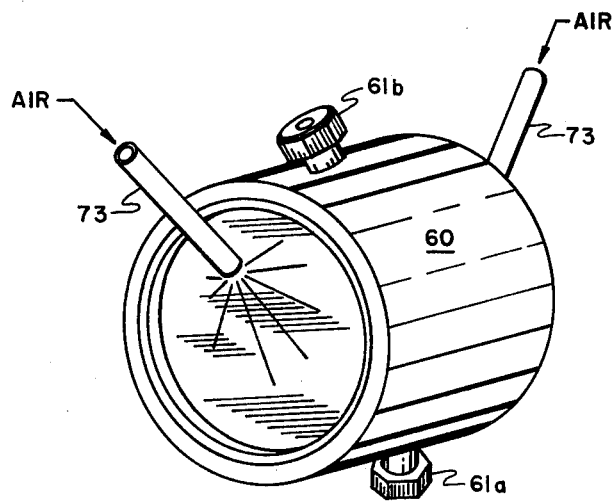
FIG. 4 is an isometric of a liquid solution monitoring photocell window unit of the present invention.

The gas photometer unit 50 illustrated by FIGS. 2 and 3 is representative also of the liquid photometer 60 illustrated by FIG. 4 with the exception of the filter 70 and the setting of the flow line inlet 51a.

Basic components of a photometer window unit are assembled within an outer ring housing 53 of Teflon or other material inert to the corrosive chlorine dioxide. On Diametrically opposite sides of the ring housing 53 are provided inlet and outlet tubing fittings 51a and 51b. It will be noted from FIG. 2 that the inlet fitting 51a of the gas window unit 50 penetrates the ring housing at an angle to the housing diameter. The objective here is for the fitting bore line to penetrate the housing 53 tangentially to the inside surface of the housing. Such tangential penetration directs the flow route of condensate droplets C away from or around the measuring light path through the window center area. This expedient of tangential penetration is unnecessary with the liquid measuring unit 60.

Symmetric about the unit center plane which includes the axes of both fittings 51a and 51b is a spacer element 55. For the gas unit 50, this element is approximately 0.5 inch (1.27 cm) wide. For the liquid unit 60, the spacer element is approximately 0.125 inch (0.32 cm) wide. In most cases the spacer unit 55 will be discontinuous about the inside surface of the housing to permit through flow between the fittings 51a and 51b.

Contiguously flanking the spacer element 55 are two clear, quartz glass window discs 54a and 54b. Compression rings 58 press O-rings 57 into the interface between the housing 53 inside surface and the outer rim of window discs 54a and 54b to pressure seal a sample space 56 between the window discs.

On the outer surface of one window disc 54b is mounted a selected blue wavelength light filter 70. For the gas unit 50, a 4400 Angstrom filter such as an Infrared Industries, Inc., 62 Forth Avenue, Waltham, Massachusetts, Model T-10-4400-100 is preferred. The liquid unit 60 perferably uses a 4600 Angstrom filter such as an Infrared industries, Inc. Model T-10-4600-100.

The particular filter frequencies disclosed have been found to provide an optimum balance of several competing circumstances. Although chlorine dioxide is considerably more absorptive and therefore more responsive of the ultraviolet spectrum below 4000 Angstroms than the blue spectrum disclosed, operational conditions tend to preclude use of 3000 to 4000 Angstrom wavelengths. Basically, large volumes of chlorine dioxide absorb too much light in the ultraviolet region thereby precluding transmittance to a photodetective receiver. Consequently, if the chlorine dioxide phase tested is liquid, the sample flow depth, i.e. thickness of the spacer element 55, required of wavelengths below 4000 Angstroms becomes so small as to render the flow stream susceptible to blockage by particulate foreign matter. On an industrial scale, flow stream cleanliness of the order required is impractical.

If the chlorine dioxide phase tested by wavelengths of less than 4000 Angstroms is gas, the reduced sample flow depth results in a sample volume that cannot tolerate the condensate film that forms on the inside surface of window discs 54 independent of condensate droplets diverted around the light path in the manner described herein.

Other prohibitions to the use of the near ultraviolet spectrum include the fact that suitably responsive photometric detectors such as silicon photocells are susceptible to ambient temperature changes. This thermal sensitivity requires either more elaborate detector circuitry to nullify such changes in the primary photocell or a thermally stabilized operational environment.

From the foregoing it will be concluded that a broad correlation is drawn between the frequency of light used for absorptive measurement and the thickness of the sampled flow stream. Experience has shown that light filters selected from the range of 4000 to 5000 Angstroms may be effectively used over a practical sample thickness range.

To detect the relative magnitude of blue light absorbed by the chlorine dioxide, a selenium photocell 71 such as a Radio Shack of Fort Worth, Texas, Stock No. 276-115 is used. This photocell 71 is mounted adjacent to the filter 70 in such a way as to restrict all incident light to that provided by the incandescent source 59 such as 15 watt lamp powered by a constant voltage transformer not shown. The transformer may be a CVS type 30 VA offered by Newark Electronics of Beltsville, Maryland.

Power leads 72 from the photocell 71 are connected to an EMF-to-current converter 74 for an appropriate signal form which is amplified for the desired transcription or control purpose. Strip chart recorder 75 is illustrated.

As previously explained, the curved, inside surface of spacer element 55 provides a flow surface for droplets C of gas line condensate around the light path area between the light source 59 and the photocell 71. Accordingly, rather than resort to elaborate schemes to remove the condensate from the gas sample flow stream, the route of such condensate through the window unit 50 is simply directed away from the sensitive area.

Photometric surveillance of the liquid chlorine dioxide line 32 is inhibited by a different form of condensate interference. Due to the fact that the chlorine dioxide solution drawn from the bottom of absorption tower 30 has been cooled to approximately 7° C., atmospheric condensate on the exterior surface of the glass discs obstructs or diffuses the light path of the liquid window unit 60 in most temperate climates. This difficulty is solved by a continuous wash flow of low pressure instrument air directed onto the exposed glass surface from a tubing conduit 73 as illustrated by FIG. 4.

Having fully described my invention and a reasonable range of variation thereof,

I claim:

1. A method of measuring the relative quantity of liquid chlorine dioxide in a flow stream comprising the steps of:
   A. Conducting said flow stream through an approximately 0.125 inch separation between transparent window means;
   B. Directing a light beam comprising wavelengths of approximately 4600 Angstrom units through said window means and flow stream into photodetector means;
   C. Filtering said light beam to permit the exclusive reception of said approximately 4600 Angstrom unit light by said photodetector means; and
   D. Correlating an electrical characteristic generated by said photodetector means to the relative quantity of chlorine dioxide in said flow stream.

2. A method of monitoring the chlorine dioxide generation rate of a process for producing same in the vapor phase in combined presence with other, contamination vapors having a greater vaporization temperature than chlorine dioxide, said method comprising the steps of:
   A. Conducting a sample flow stream of said combined vapors through an approximately 0.50 inch separation space between transparent windows;
   B. Directing a light beam comprising wavelengths of approximately 4400 Angstroms through said windows, a sample of said combined vapors within said space therebetween and into photodetector means;
   C. Filtering said light beam to permit the exclusive reception of said approximately 4400 Angstrom light by said photodetector means; and
   D. Correlating an electrical characteristic generated by said photodetector means to the relative quantity of chlorine dioxide in said flow stream.

3. A method as described by claim 2 wherein condensed contaminates in said flow stream are routed around said light beam through said windows.

4. A method as described by claim 2 wherein said sample flow stream is maintained at a substantially constant downward slope between a vapor entrance point thereof and said windows.

5. A method as described by claim 4 wherein movement of said sample flow stream is induced by aspiration.

6. An apparatus for measuring the relative quantity of gaseous chlorine dioxide in a mixed phase fluid comprising:
   A. A volumetric sample space having oppositely facing transparent sidewalls disposed within a flow stream of said fluid;
   B. A source of approximately 4400 Angstrom wavelength light directed through said sidewalls and an approximately 0.50 inch depth of said sample space from one side thereof; and,
   C. Photodetector means disposed on the other side of said sidewalls to receive said 4400 Angstrom light exclusively and generate an electrical characteristic responsive thereto.

7. An apparatus as described by claim 6 comprising a circular sample space between said sidewalls and entrance and exit flow conduit means penetrating said sample space at substantially diametric opposite locations, said entrance flow conduit means entering said sample space substantially tangent to the circular periphery thereof.

8. An apparatus as described by claim 7 wherein said fluid is substantially vaporous and aspiration means is provided in said exit flow conduit means to induce said vaporous fluid flow through said sample chamber.

9. A photometer window for photometrically sampling the gas constituent of a mixed phase fluid flow stream, said window comprising:
   A. Hollow barrel means disposed between opposite face planes of two transparent window means, said hollow barrel means having a closed periphery, substantially continuous, interior wall portion symmetrically disposed about a sight axis passing therethrough perpendicular to said window means face planes; and,
   B. Inlet and outlet fluid flow conduit means penetrating said wall portion at substantially opposite locations relative to said axis, said inlet conduit penetrating said interior wall with a smooth, substantially tangent angular relationship therewith.

* * * * *